United States Patent [19]

Hunsaker et al.

[11] Patent Number: 5,564,108
[45] Date of Patent: Oct. 8, 1996

[54] NON-INVASIVE SOFTWARE UPDATE APPARATUS

[75] Inventors: Scott W. Hunsaker, Boulder; Stephan Kulik, III, Louisville; Alan D. Martin, Lafayette; Craig A. Totel, Westminster, all of Colo.

[73] Assignee: Ohmeda Inc., Liberty Corner, N.J.

[21] Appl. No.: 439,718

[22] Filed: May 12, 1995

Related U.S. Application Data

[63] Continuation of Ser. No. 114,703, Aug. 31, 1993, abandoned.

[51] Int. Cl.$^6$ ............................................. G06F 13/00
[52] U.S. Cl. ..................... 395/800; 395/836; 364/550; 364/413.02; 364/413.03
[58] Field of Search ........................... 395/800, 500; 364/DIG. 1, 510, 413.02, 413.03, 224.6, 550; 128/633, 713; 307/518; 340/522, 521

[56] References Cited

U.S. PATENT DOCUMENTS

| | | | |
|---|---|---|---|
| 4,350,858 | 9/1982 | Yoshida | 219/10.55 B |
| 4,736,193 | 4/1988 | Slocum et al. | 340/522 |
| 4,740,777 | 4/1988 | Slocum et al. | 340/522 |
| 4,750,136 | 6/1988 | Arpin et al. | 364/514 |
| 4,835,521 | 5/1989 | Andrejasich et al. | 340/521 |
| 4,862,355 | 8/1989 | Newman et al. | 364/DIG. 1 |
| 4,892,101 | 1/1990 | Cheung et al. | 128/633 |
| 4,916,339 | 4/1990 | Lloyd | 307/518 |
| 5,046,505 | 9/1991 | Sekii et al. | 128/713 |
| 5,155,356 | 10/1992 | Peters et al. | 250/253 |
| 5,195,130 | 3/1993 | Weiss et al. | 379/98 |
| 5,214,771 | 5/1993 | Clara et al. | 395/500 |
| 5,218,554 | 6/1993 | Slocum | 364/510 |
| 5,259,381 | 11/1993 | Cheung et al. | 128/633 |
| 5,376,927 | 12/1994 | Kidd | 340/522 |
| 5,437,044 | 7/1995 | Hohner et al. | 395/800 |
| 5,455,766 | 10/1995 | Scheller et al. | 364/413.01 |

*Primary Examiner*—Alyssa H. Bowler
*Assistant Examiner*—Walter D. Davis
*Attorney, Agent, or Firm*—Roger M. Rathbun; Larry R. Cassett; James M. Graziano

[57] ABSTRACT

This apparatus makes use of the existing data collection probe connector on the instrumentation as the port through which the software updates are loaded into the programmable memory devices that are used to store the operational software of the instrumentation. Circuitry is provided in the instrumentation to automatically differentiate between software update data being loaded into the instrumentation and the normal monitoring data that is received from the probe. This is accomplished by the use of probe defining circuitry that is able to differentiate between the standard probe used for data collection purposes and the software update probe that is provided to download software into the programmable memory devices.

18 Claims, 3 Drawing Sheets

NON-INVASIVE SOFTWARE UPDATE APPARATUS

This is a continuation of application Ser. No. 08/114,703 filed Aug. 31, 1993, now abandoned.

FIELD OF THE INVENTION

This invention relates to processor-controlled instrumentation and, in particular, to apparatus for non-invasively updating the software of a processor-controlled medical monitoring apparatus.

PROBLEM

It is a problem in the field of instrumentation to update on a regular basis the operational computer program that is contained therein. The software used to control the operation of instrumentation is stored in non-volatile memory, since the instrumentation may be maintained in a power down condition for an extended period of time. Therefore, the software is in the form of program instructions stored in read only memory or a programmable read only memory.

In the case of read only memory, software updates can be accomplished only by replacing the memory devices, which entails disassembling the equipment. This software update operation requires an extensive amount of time and removes the instrumentation from service for the duration of the update process, which can be a significant impediment if the instrumentation is used on a continuous basis.

If the memory devices are programmable read only memory, the devices need not be removed from the equipment to have the software updated. However, to provide access to the programmable read only memory, the instrumentation must be equipped with a separate connector that is used solely for the purpose of updating the software. The provision of an extra connector represents a significant design problem in many instrumentation applications due to the limited amount of space available on the front and back panels of the equipment. This problem is further exacerbated when the instrumentation is part of a rack mounted system and represents a pluggable module that must interface with an aperture in the rack mounted system of predetermined dimensions and having a connector of predetermined configuration. In this environment, the user or the repair person may only have access to the front panel of the equipment which is typically occupied by displays, controls and plugs for the probes that are used to connect to the subject being monitored. In this application, no space is available to provide a separate connector for the purpose of software update of a programmable memory device.

In the field of medical monitoring apparatus, the instrumentation may be in substantially continuous use and cannot be removed from use for a significant amount of time to provide software updates. Therefore, much of the medical monitoring apparatus presently used does not receive updates to the software on a frequent or regular basis.

SOLUTION

The above-described problems are solved and a technical advance achieved in the field by the non-invasive software update apparatus of the present invention. This apparatus makes use of the existing monitoring probe connection on the instrumentation as the port through which the software updates are loaded into the programmable memory devices that are used to store the operational software of the instrumentation. Apparatus is provided in the instrumentation to automatically differentiate between software update data being loaded into the instrumentation and the normal monitoring data that is received from the monitoring probe. This is accomplished by the use of probe defining apparatus that is able to differentiate between the standard monitoring probe used for data collection purposes and the software update probe that is provided to download software into the programmable memory devices.

One method of defining the probe used with the instrumentation is to provide a passive device, such as a resistor, in the probe, the characteristics of which can be determined by the instrumentation. An example of this is found in the field of pulse oximetry, wherein the pulse oximeter probe contains light-emitting diodes and light detectors for measuring the characteristics of certain components of the arterial blood. In order to differentiate between the plurality of possible light-emitting diode characteristics, a resistor is included in the probe, the value of which is indicative of the type of light-emitting diodes used in that probe. The pulse oximeter instrument queries the probe by measuring the resistance of the coding resistors and adjusts the computational factors to correspond to the characteristics of the particular light-emitting diodes found in that probe. An alternative embodiment of this probe makes use of a memory device located in the probe to identify the probe characteristic. The "smart probe" contains a memory device that stores a serially accessed data structure which holds the operational parameters of the probe. This probe is queried using a data inquiry communication protocol.

The non-invasive software update apparatus, as disclosed in the preferred embodiment, makes use the fact that passive coding resistor probe differentiation apparatus does not respond if queried by a data inquiry communication protocol. The non-invasive software apparatus therefore queries the probe using this protocol to differentiate between a software update probe and a standard monitoring probe. If there is no response, a passive resistor probe identification is presumed to be present in the probe. If the probe responds to this inquiry in the proper protocol, a software update probe or a smart probe is present and these can be differentiated by the content of the response. This form of probe differentiation enables the non-invasive software update apparatus to identify the presence of a software update probe. This enables the software in the instrumentation to be updated by simply plugging the instrumentation, via a cable that properly responds to the inquiry, to a software update device which can be as simple as the user's personal computer or a portable lap-top computer that is transported to the instrumentation site by a craftsperson. In this manner, the software stored in the instrumentation can be updated in a matter of moments without requiring disassembly of the instrumentation and exchange of components contained therein. The instrumentation does not even have to be removed from its operational location, such as in a rack-mounted installation. In this manner, software updates can be propagated to the instrumentation in the field in a manner that is cost effective.

This non-invasive software update apparatus is also beneficial for use in the manufacturing process where manufacturing test software can be selectively loaded into the program memory during the manufacture of the processor control instrumentation to perform test operations during the manufacturing process. As the processor controlled instrument proceeds through the manufacturing and assembly process, the software contained therein can be simply modified using the non-invasive software update apparatus to provide assembly test specific test procedures without requiring the manufacturing personnel to exchange memory devices in the instrument. Once the manufacturing process has been completed, the manufacturing test software can be removed from the processor controlled instrument by writing the operational software therein using the non-invasive software update apparatus. Additionally, operational tests can be performed at the installation site by loading test procedures into memory using the non-invasive software update apparatus to perform specific diagnostic routines, upon the completion of which the diagnostic software is removed from the program memory. Thus, the non-invasive software update apparatus provides a facility to quickly and simply load additional software into the processor controlled instrumentation to perform application-specific operations during the product life.

DETAILED DESCRIPTION

Figure 1:
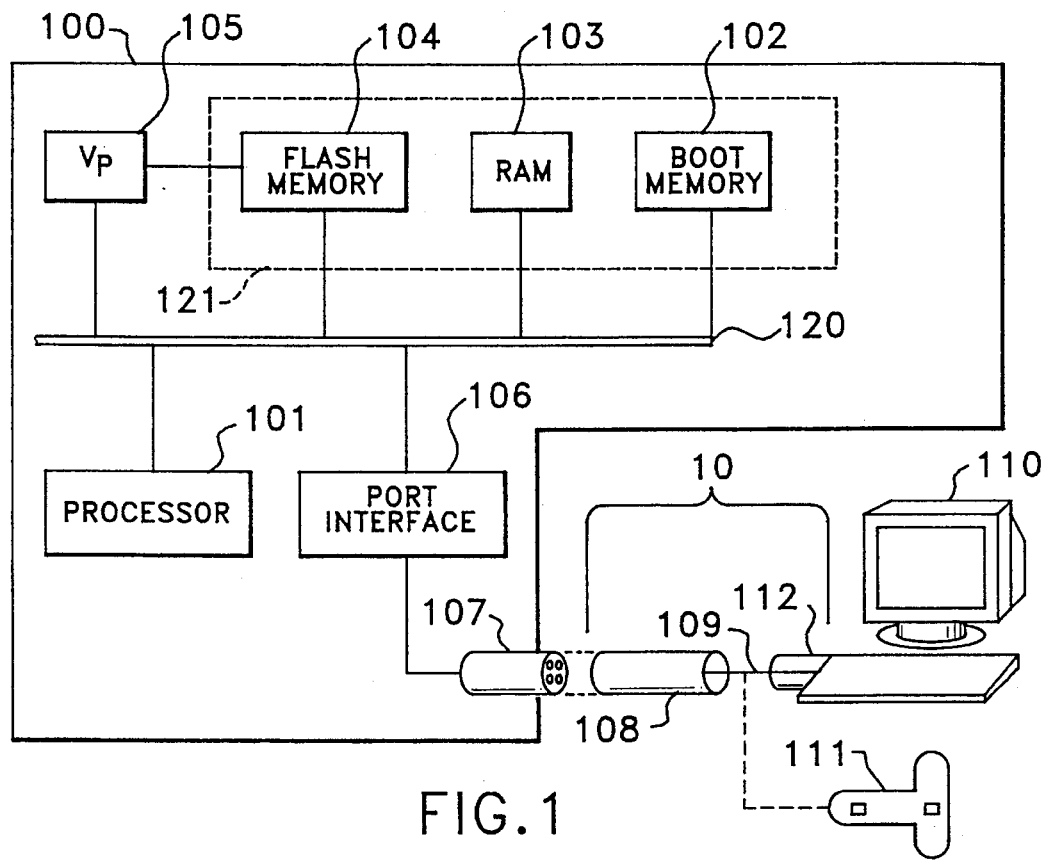
FIG. 1 illustrates in block diagram form the overall architecture of the non-invasive software update apparatus of the present invention.

FIG. 1 illustrates in block diagram form the overall architecture of the non-invasive software update apparatus of the present invention as well as an application of this apparatus in monitoring instrumentation. For illustrative purposes, the disclosed embodiment is selected to be a medical monitoring instrument, such as a pulse oximeter, that is mounted in a rack with a plurality of other instrumentation in an environment that renders equipment maintenance difficult, such as an operating room in a hospital. In this environment, the instrumentation is in fairly continuous use, and any software updates that require removal of the instrumentation from the rack and disassembly of the instrumentation to replace the memory devices contained therein are both time-consuming and disruptive of the use of not only the instrumentation, but also the operating room facility itself. These constraints therefore render the prior art software update process impractical for all but major software revisions that are necessitated by significant performance factor improvements. In the past, software updates for instrumentation in this and other like environments were infrequently or never provided due to the cost of implementing the software update.

System Architecture

The non-invasive software update apparatus is included in a processor controlled instrumentation which, for the purpose of this description is presumed to be a medical monitoring apparatus, such as a pulse oximeter system as shown in FIG. 1. The monitoring system 100 includes a processor 101 that functions under software control to perform certain measurements. In the case of a pulse oximeter system, a probe 111 is attached by cable 109 that is terminated in connector 108 to a port 107 on monitoring system 100. This connection is illustrated in dotted line form to indicate that it is the usual use of the monitoring system 100 but not the non-invasive software update application described herein.

Port interface circuit 106 provides drive signals to obtain measurement data from sensors that are located in probe 111 to perform the required measurements on the subject to which probe 111 is attached. In the case of the probe oximeter, light source and light detector devices are used to perform a photoplethysmographic determination of the oxygen content of the arterial hemoglobin that is found in a patient's appendage. In a typical application, probe 111 is a conformable pad that is wrapped around a patient's finger to place a light sources on one side of the finger and a light detector on the other side of the finger. Drive signals are transmitted from the port interface circuit 106 via cable 109 to the light source on probe 111 to illuminate the patient's finger. The light transmitted through the arterial bed of the finger is measured by the light detector contained in probe 111 and the analog signal indicative of this measurement is transmitted on cable 109 to the port interface circuit 106. Processor 101 is connected to port interface circuit 106 via bus 120 and operates to translate the received data indicative of the magnitude of the light beam that is transmitted through the patient's finger into an indication of the oxygen content of the hemoglobin contained in the patient's arterial blood flow.

Processor 101 operates under control of a series of program instructions that are stored in memory 121. In the apparatus of the present invention, memory 121 can consist of a plurality of memory devices. An optional boot memory 102 is provided and consists of a non-volatile memory, which can be flash memory device(s), in which is stored the basic operational software 101 to perform the elemental processor functions. A random access read/write memory 103 is provided and consists of the processor's work space where the data and computational results are temporarily stored during the measurement process. A program memory 104, which can be flash memory device(s), is also included in memory 121 and consists of the repository of program instructions that are used by processor 101 to perform its designated function which, in this case, is the monitoring of a physiological characteristic of a patient. These individual memory elements are shown for illustrative purposes and various combinations of memory elements or even a single memory element can be used to implement memory 121. Flash memory devices consist of a non-volatile memory that can be reprogrammed while physically located in monitoring system 100. A source 105 of reprogramming voltage is connected to flash memory and operates under control of processor 101 to selectively erase program instructions that are stored in flash memory. The reprogramming voltage may be the standard supply voltage of monitoring system 100 or may be a predefined voltage generated by additional circuitry that is included in source 105, as necessitated by the specific selection of the devices used to implement the flash memory.

Due to the difficulty in providing a program instruction input port on a medical monitoring apparatus, such as monitoring system 100, the standard data collection port 107 is used for the dual purpose of data acquisition using sensor 111 and software update data collection which is accomplished by using a source of program instructions such as a lap top or portable computer 110. Alternatively, a dial up phone connection (not shown) can be implemented in lieu of computer 110 to provide a source of program instructions for monitoring system 100. In any case, the connector 108 that is plugged into port 107 can be interconnected by cable 109 to either a standard sensor probe 111 or a source of program updates 110.

Partitioned, Non-Volatile Reprogrammable Memory

The flash memory devices 104 used for program memory and optionally boot memory 102 illustrated in FIG. 1 are implemented by a partitioned, non-volatile and reprogrammable device that is used to store the basic program instructions used by processor 101 to control the operation of monitoring system 100. The flash memory is a non-volatile memory which holds its contents when power to the device is removed. A feature of this device is that it can be partitioned to allow some or all parts of the memory to be write-protected to prevent the program instructions that are stored therein from being erased by the software update process. The partitions of this memory that are not write-protected can be reprogrammed by means of erasing the program instructions that are stored in those memory locations contained in the partition of memory that is not write-protected and new program instructions can be written therein in place of the previously stored and now erased program instructions. These instructions are then downloaded to the random access memory 103 for execution by processor 101. There are a number of partitioned, non-volatile reprogrammable memory devices presently on the market, one of which is manufactured by Advanced Micro Devices Corporation and sold under the code number Am29F010, and another device is manufactured by Intel under the product name ETOX II. The flash memory is reprogrammed by electrically erasing all the data bits in parallel in a segment of the memory and then programming data into in the erased portion of the array. The programming operation is achieved either by use of a set of program instructions that can be stored in the boot memory 102 program memory 104 or by downloading these instructions to random access memory 103 as part of the software update process. The data can be written into the program memory 104 in any data width and the source of the information can be either a serial or a parallel communication link to a source of program instruction data. In the system illustrated in FIG. 1, a serial communication channel is used consisting of port 107 and port interface circuit 106 which is shown in additional detail in FIG. 202.

Program Instruction Input

In order to use port 107 for the dual functions of sensor data acquisition and program instruction downloading, there must be some means of differentiating the two types of data in an automatic fashion to unerringly store each type of data in its appropriate location. To accomplish this, port interface circuit 106 automatically identifies the nature of the probe that is connected to port 107. In the case of a resistor coded probe as the standard probe for monitoring system 100, the sensor probe 111 has certain impedance characteristics that are differentiable from the impedance characteristics of a source of program instructions, such as computer 110. The impedance measurement circuitry contained in port interface circuit 106 responds to the connection of a probe to port 107 by measuring the impedance characteristics of the connected probe and comparing the results to data stored in port interface circuit 106 to identify the type of probe that is connected to port 107. In the instance of computer 110 being connected to port 107, probe interface circuit 106 indicates to processor 101 that the data that is input to system 100 via port 107 consists of control data and program instructions that are received from computer 110. In the case of a "smart probe", a memory device in the probe contains data indicative of the probe characteristics. The monitoring system 100 queries this memory via a data inquiry communication protocol. The inquiry can differentiate between monitoring probe 111 and computer 110 based upon the response that is received from the inquiry.

Figure 2:
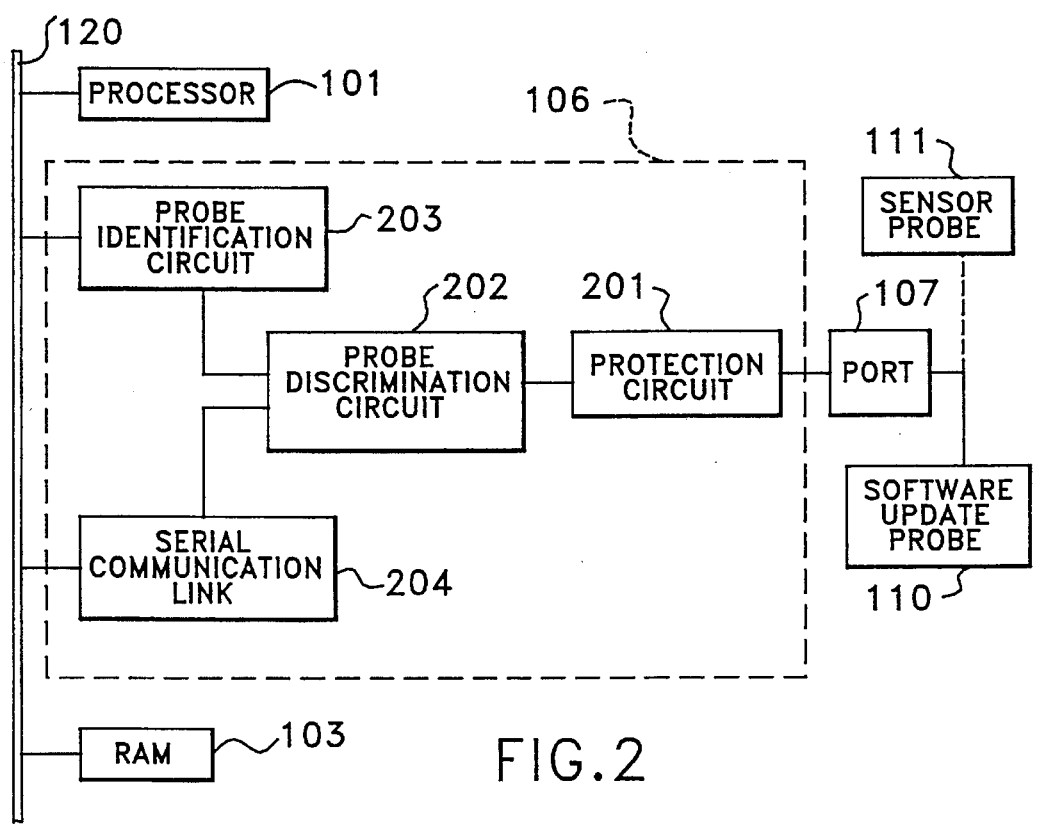
FIGS. 2 and 3 illustrate additional details of the probe interface circuitry.
Figure 3:
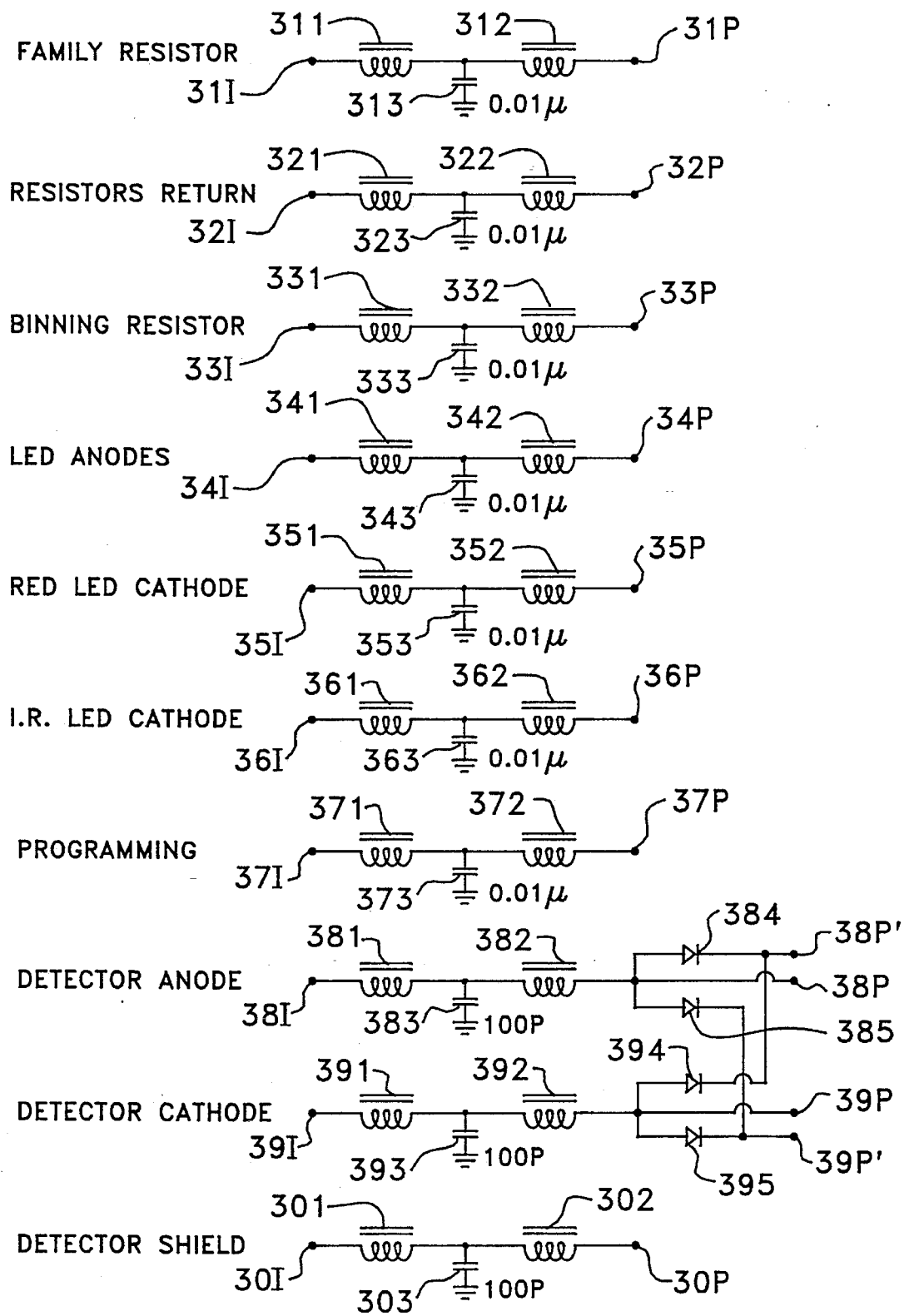
Figure 4:
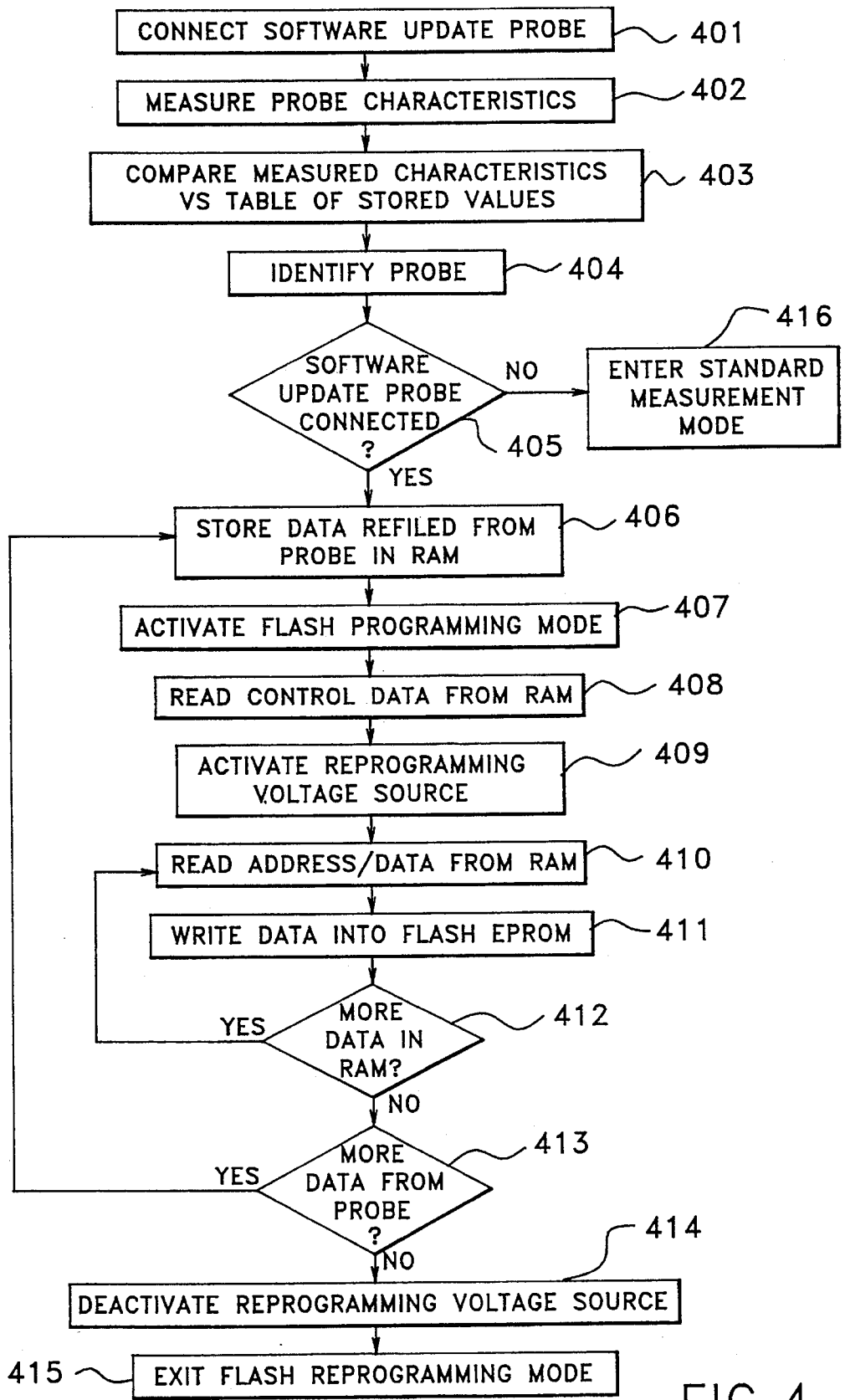
FIG. 4 illustrates in flow diagram form the operational steps taken by the non-invasive software update apparatus to modify the software that is stored in the programmable apparatus.

The flow diagram of FIG. 4 illustrates the operational steps taken by the non-invasive software update apparatus to accomplish the probe differentiation and program instruction storage functions. At step 401, a user connects the software update probe 10 to port 107, wherein the software update probe 10 consists of a connector 108 that mates with port 107. Connector 108 terminates cable 109, which is connected at the distal end thereof via connector 112 to a source of program instructions, such as computer 110 or a telecommunications connection to a remotely located computer. At step 402, in response to the interconnection of a probe to port 107, port interface circuit 106 performs a set of measurement to identify the predetermined characteristics of the probe that is connected to port 107. In the specific embodiment that is illustrated in FIGS. 1–3, the port interface circuit 106 determines the characteristics of the probe that is connected to port 107. At step 403, port interface circuit 106 compares the determined characteristics with a set of data that are stored in a memory. Based on the correspondence between the determined characteristics and the entries stored in the memory, port interface circuit 106 can identify the probe connected to port 107. At step 405, port interface circuit 106 makes a determination whether a software update probe is connected to port 107. If not, at step 416, processor 101 enters a standard data acquisition mode that is controlled by the program instructions stored in program memory 104 and used to translate the data received from sensor probe 111 into the oxygen content measurements noted above. If, however, at step 405, processor 101 determines that the software update probe 10 is connected to port 107, at step 406 processor 101 stores the data that is received from port 107 in random access memory 103 for use in reprogramming program memory 104.

At step 407, processor 101 activates the flash memory programming mode. The specific reprogramming steps and their sequences are determined by the device used to implement the flash memory, and the description provided herein is illustrative of the general process. At step 408, processor 101 reads any control data that is included in the data that is input to monitoring system 100 via port 107 by the software update computer 110. At step 409, processor 101 activates the source 105 of reprogramming voltage which applies an elevated voltage (if required) to an appropriate terminal of program memory 104 to automatically erase the memory contents from the unprotected partitions of program memory 104. Upon completion of this data erasure process, at step 410, processor 101 reads data from random access memory 103 along with corresponding address information. At step 411, processor 101 transmits the data read from access memory 103 via bus 120 to the address and data terminals of program memory 104 to store these new program instructions therein. At step 412, processor 101 determines whether additional program instructions are stored in random access memory 103 for loading into program memory 104. If so, processing returns to step 410 and steps 410–412 are repeated until all the program instructions received from computer 110 have been written into program memory 104.

Once no more instructions remain to be loaded into program memory 104, from random access memory 103, processing proceeds to step 413 where processor 101 determines whether additional program instructions are to be received from software update computer 110. If so, processing returns to step 406 and if not, processor 101 deactivates the programming voltage source 105 at step 414, exits the flash programming mode and returns to normal data programming acquisition processing at step 415.

Probe Interface Circuit

To make this non-invasive software process a viable capability on a medical monitoring instrument such as monitoring system 100, port 107 must be shared between the data acquisition function and the software update function. To accomplish this result in a reliable yet simple manner, the sensor probe port 107 is used to interconnect computer 110 to monitoring system 100. An identical connector 108 is used for both functions and the differentiation between the sensor probe 111 and the computer 110 is accomplished by the circuitry illustrated in FIG. 2.

A typical sensor probe 111 includes two light sources and a light detector that are use to illuminate the patient's appendage and measure the light transmission through the arterial bed to determine the oxygen content of the hemoglobin contained in the patient's arterial blood flow. Also included in sensor probe 111 is a probe identification apparatus which consists of a pair of resistors or a memory device that are used to identify the operational characteristics of the two light emitting diodes. The data stored in the probe memory device or the impedance value of each of the resistors identifies a particular wavelength spectrum at which the corresponding light sources operate. Probe discrimination apparatus 202 in port interface circuit 106 determines whether a sensor probe 111 or a software update probe is present. Probe identification circuit 203, in response to the presence of sensor probe 111 reads the data obtained from the probe memory device or the determined impedance value of these two resistors or uses this data to identify the specific characteristics of the light sources to processor 101 which adjusts its computational functions to account for variations in light source characteristics that are provided in sensor probe 111.

The software update apparatus makes use of this probe identification capability to distinguish the software update probe from the sensor probe 111. This is accomplished either by placing coding resistors whose values do not correspond to any of the standard light source identification resistors in the software update probe or by providing a data query response. The resistors can be placed in connector 108 or in connector 112 such that the impedance determination circuitry in port interface circuit 106 can measure the impedance of these resistors and by means of the look-up table differentiate the software update probe from the sensor probe 111. Therefore, the software update probe 10 consists of a connector 108 that mates with port 107. Connector 108 functions to terminate one end of a cable 109 the other end of which is terminated in a connector 112 that corresponds to a port (not shown) on computer 110. Thus, the software update probe 10 simply consists of a cable with two connectors one end of which is connected to port 107, the other end of which is connected to a source of data including program instructions. The preferred embodiment of the software update probe 10 emulates the operation of a "smart probe" and responds to a query transmitted to it in a data inquiry communication protocol. In this configuration, probe discrimination circuit 202 transmits a query in a predefined data inquiry communication protocol to the probe connected to port 107. A smart probe responds to the query by transmitting probe identification data from its memory device to probe discrimination circuit 202, which determines from the nature of this data that a smart probe is present at port 107. The received data is then forwarded to probe identification circuit 203 for use, as noted above, in identifying the characteristics of the light-emitting devices in sensor probe 111.

If probe discrimination circuit 202 determines that a header is received at port 107 in response to the query that was transmitted to the probe, the received data is switched by probe discrimination circuit 202 to serial communication link 204 which functions to receive the input digital data stream. The serial communication link 204 interfaces the data inquiry communication protocol and forwards the received data to random access memory 103 under control of processor 101. Processor 101 excerpts any control instructions from this input data stream that are required to process the input data.

Protected Interface

Monitoring system 100 is a medical monitoring apparatus and, as such, is required by safety regulations to safeguard the user from hazardous voltages and currents. In addition, monitoring system 100 is operational in an environment that can contain numerous sources of electro-magnetic interference (EMI) and monitoring system 100 must not itself radiate EMI. Therefore, the parameter that is being measured can easily be obliterated by the electro-magnetic interference caused by the concurrent operation of other medical instrumentation. The interface that interconnects the sensor probe 111 must filter this external spurious noise, suppress noise generated by the monitoring system 100, while at the same time protecting the patient from voltage and currents that can be harmful. To accomplish this requires the use of EMI filter circuitry and voltage and current protective circuitry which add a significant expense to the implementation of this interface. There is therefore a significant financial incentive to make use of port 107 for the data acquisition as well as software update inputting functions, and any software updating port would require the same protective circuit that is used on port 107.

Port interface 106 includes a protection circuit 201, one embodiment of which is illustrated in additional detail in FIG. 3. Port 107 includes a plurality of signal conductors and, for the purpose of description, ten probe conductors 311–301 are shown in FIG. 3. Each of the probe conductors 311–301 is connected to an element contained in sensor probe 111, the identity of which is listed in FIG. 3 next to the corresponding conductor. Each probe conductor **3\*I is connected via corresponding protection circuitry 3\*1–3\*3 to an output conductor 3\*P that is connected to monitoring circuitry, as is well-known in the art, in monitoring system 100**.

The protection circuits illustrated in FIG. 3 consist of a pair of series connected inductors **3\*1, 3\*2 that are connected to a corresponding probe conductor 3\*I and output conductor 3\*P, respectively. A capacitor 3\*3 is connected between the junction of the two inductors 3\*1, 3\*2 and circuit ground to form an inductive T filter to suppress EMI. In addition, a bridge rectifier consisting of diodes 384, 385, 394, 395 is connected across output leads 38P, 39P to provide an output on leads 38P', 39P'**.

This protection circuit is simply one of the many possible configurations that can be used to reduce EMI on the signals received at port 107. As noted above, the expense of providing protection circuit 201 and the space limitation on the equipment for additional connectors weighs heavily in favor of multiple uses for port 107, which capability is provided by the non-invasive software update apparatus.

It is expressly understood that the claimed invention is not to be limited to the description of the preferred embodiment but encompasses other modifications and alterations within the scope and spirit of the inventive concept.

We claim:

1. Apparatus for automatically writing program instructions into a program memory, which is used to store program instructions that regulate operation of a processor, which is located in a processor controlled parameter measuring system, where said parameter measuring system is equipped with a port that receives a data collection probe used to collect sensor data to enable said processor to measure a parameter whose characteristics are monitored by said data collection probe connected to said port, comprising:

means, connected to said port, for automatically determining whether said data collection probe is connected to said port;

means, responsive to said determining means indicating that said data collection probe is connected to said port, for receiving data input to said port as sensor data for use by said processor to measure said parameter whose characteristics are monitored by said data collection probe:

means, responsive to said determining means indicating that said data collection probe is not connected to said port, for receiving data input to said port as program instructions for use by said system to regulate the operation of said processor; and means for storing said received program instructions in said program memory.

2. The apparatus of claim 1 wherein said determining means comprises:

means for measuring a physical characteristic of a probe connected to said port; and means for comparing said measured physical characteristic with data stored in a memory to determine whether said data collection probe is connected to said port.

3. The apparatus of claim 2 wherein said data collection probe includes a resistor of predetermined impedance, said measuring means determines an impedance of a probe connected to said port; and said comparing means compares said measured impedance with data stored in a memory to determine whether said data collection probe is connected to said port.

4. The apparatus of claim 1 wherein said determining means comprises:

means for transmitting a query, in a predefined protocol, to a probe connected to said port; and means, responsive to a response from said probe in said predefined protocol, for determining that said data collection probe is not connected to said port.

5. The apparatus of claim 1 wherein measurement data is input to said port via a data collection probe using a predetermined protocol, said determining means comprises:

means for transmitting a query in said predetermined protocol to a probe connected to said port; and means for determining that said data collection probe is connected to said port from a content of a response in said predetermined protocol received at said port in response to said query.

6. The apparatus of claim 1 wherein said program memory comprises a programmable read only memory, said storing means comprises:

means for writing said received program instructions in said programmable read only memory.

7. The apparatus of claim 1 wherein said data is input to said port via a software update probe and said data comprises control data and program instructions, said storing means further comprises:

means for interpreting said control data to identify memory locations in said program memory in which to store said program instructions contained in said data received at said port.

8. The apparatus of claim 1 wherein said apparatus further comprises a software update probe that comprises a cable, one end of whim is pliable into said pod and another end of which is connectable to a source of data indicative of said program instructions.

9. The apparatus of claim 1 wherein said storing means comprises:

means, responsive to data received at said port from a source of data, for storing said data in a buffer memory;

means for excerpting software changes from said stored data;

means for inputting said excerpted software changes into said program memory.

10. The apparatus of claim 9 wherein said program memory comprises a flash EPROM, said inputting means comprises:

EPROM burn means for fixing said software changes in said EPROM.

11. A method for automatically inputting software changes into a program memory, which is used to store program instructions that regulate operation of a processor, which is located in a processor controlled parameter measuring equipment, wherein said processor controlled equipment includes a port for connection to a data collection probe to collect sensor data to enable said processor to measure a parameter whose characteristics are monitored by said data collection probe connected to said port, comprising the steps of:

interconnecting said port to a source of data;

automatically determining whether said data collection probe is connected to said port;

receiving, in response to said step of determining indicating that said data collection probe is connected to said port, data input to said port as sensor data for use by said processor to measure said parameter whose characteristics are monitored by said data collection probe;

identifying, in response to said step of determining indicating that said data collection probe is not connected to said pod, a source of program instructions being connected to said port; and automatically storing said program instructions received at said port in said program memory.

12. The method of claim 11 wherein said data collection probe has a predefined impedance characteristic, said step of identifying comprises:

differentiating an impedance of said source of data from said data collection probe impedance characteristic.

13. The method of claim 12 wherein said step of differentiating comprises:

measuring an impedance of an element connected to said port;

comparing said measured impedance to data indicative of said impedance of said source of data and said data collection probe impedance characteristic to identify tho one of said data collection probe and said source of data connected to said port.

14. The method of claim 11 wherein said step of identifying comprises:

transmitting a query, in a predefined protocol, to a probe connected to said port; and determining, in response to receipt of a response from said probe in said predefined protocol, that said source of data is connected to said port.

15. The method of claim 11 wherein measurement data is input to said port via a data collection probe using a predetermined protocol, said step of identifying comprises:

transmitting a query in said predetermined protocol to a probe connected to said port; and determining that said software update probe is connected to said port from a content of a response in said predetermined protocol received at said port in response to said query.

16. The method of claim 11 wherein said source of data is connectable to said port via a cable, one end of which is pluggable into said port and another end of which is connected to said source of data.

17. The method of claim 11 wherein said step of storing comprises:

storing, in response to data received at said port from said source of data, said data in a buffer memory;

excerpting software changes from said stored data;

inputting said excerpted software changes into said program memory.

18. The method of claim 17 wherein said program memory comprises a flash EPROM, said step of inputting comprises:

burning said software changes in said EPROM.

* * * * *